United States Patent
Dunning et al.

(10) Patent No.: US 10,729,486 B2
(45) Date of Patent: Aug. 4, 2020

(54) IMPLANT MODE FOR ELECTROSURGICAL GENERATOR

(71) Applicant: COVIDIEN LP, Mansfield, MA (US)

(72) Inventors: James E. Dunning, Lafayette, CO (US); Sara E. Anderson, Longmont, CO (US); Steven P. Buysse, Niwot, CO (US)

(73) Assignee: Covidien LP, Mansfield, MA (US)

( * ) Notice: Subject to any disclaimer, the term of this patent is extended or adjusted under 35 U.S.C. 154(b) by 792 days.

(21) Appl. No.: 15/244,161

(22) Filed: Aug. 23, 2016

(65) Prior Publication Data

US 2018/0055556 A1    Mar. 1, 2018

(51) Int. Cl.
*A61B 18/00* (2006.01)
*A61B 18/12* (2006.01)
(Continued)

(52) U.S. Cl.
CPC ........ *A61B 18/1233* (2013.01); *A61B 5/0031* (2013.01); *A61B 5/686* (2013.01); *A61N 1/36142* (2013.01); *A61N 1/3718* (2013.01); *A61N 1/3931* (2013.01); *A61B 18/1206* (2013.01); *A61B 18/1445* (2013.01); *A61B 18/1477* (2013.01); *A61B 18/1482* (2013.01); *A61B 2018/0063* (2013.01); *A61B 2018/0072* (2013.01); *A61B 2018/00577* (2013.01); *A61B 2018/00601* (2013.01); *A61B 2018/00607* (2013.01); *A61B 2018/00636* (2013.01); *A61B 2018/00642* (2013.01);
(Continued)

(58) Field of Classification Search
CPC .. A61B 2018/1293; A61B 2018/00642; A61B 2018/00577; A61B 2018/00601; A61B 2018/00607; A61B 2018/0063; A61B 2018/00636; A61B 2018/00702; A61B 2018/00726; A61B 2018/00732; A61B 2018/00767; A61B 2018/00988; A61B 18/1233; A61B 18/1206; A61B 18/1445; A61B 18/1477; A61B 18/1482; A61B 5/686; A61B 5/0031; A61N 1/36142; A61N 1/3718
See application file for complete search history.

(56) References Cited

U.S. PATENT DOCUMENTS 5,697,958 A    12/1997  Paul et al.
6,678,560 B1   1/2004   Gilkerson et al.
(Continued)

OTHER PUBLICATIONS

Extended European Search Report for application No. 17187177.5 dated Jan. 4, 2018 (5 pages).

*Primary Examiner* — Jaymi E Della
*Assistant Examiner* — Rachel A. Vierra
(74) *Attorney, Agent, or Firm* — Carter, DeLuca & Farrell LLP

(57) ABSTRACT

Disclosed are devices, systems, and methods for operating an electrosurgical generator, including a radio-frequency (RF) output stage configured to output an electrosurgical waveform, a wireless transceiver configured to communicate with an implantable device in a patient, and a controller coupled to the RF output stage and the wireless transceiver, the controller configured to control the RF output stage to generate an electrosurgical waveform based on the implantable device.

19 Claims, 8 Drawing Sheets

(51) Int. Cl.
    *A61N 1/36*           (2006.01)
    *A61N 1/37*           (2006.01)
    *A61N 1/39*           (2006.01)
    *A61B 5/00*           (2006.01)
    *A61B 18/14*          (2006.01)

(52) U.S. Cl.
    CPC .............. *A61B 2018/00702* (2013.01); *A61B 2018/00726* (2013.01); *A61B 2018/00732* (2013.01); *A61B 2018/00767* (2013.01); *A61B 2018/00988* (2013.01); *A61B 2018/1293* (2013.01)

(56) References Cited

U.S. PATENT DOCUMENTS

| | | |
|---|---|---|
| 8,761,717 B1 | 6/2014 | Buchheit |
| 2006/0074455 A1 | 4/2006 | Strandberg |
| 2007/0198007 A1* | 8/2007 | Govari .............. A61B 18/1492 606/34 |
| 2012/0165811 A1* | 6/2012 | Gillberg .............. A61N 1/3621 606/41 |
| 2012/0310241 A1* | 12/2012 | Orszulak ................ A61B 18/12 606/51 |
| 2013/0165918 A1 | 6/2013 | Riff |
| 2016/0015992 A1 | 1/2016 | Whitlock |

\* cited by examiner

IMPLANT MODE FOR ELECTROSURGICAL GENERATOR

BACKGROUND

Technical Field

The present disclosure relates to systems and methods for controlling an electrosurgical generator configured to generate a radio frequency ("RF") waveform having a plurality of RF cycles for treating tissue. In particular, the present disclosure relates to an electrosurgical generator having a plurality of output modes that can be selected based on devices attached to or implanted in a patient.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Electrosurgical energy may cause interference with implantable devices disposed in the body of a patient undergoing electrosurgery. For example, electrosurgical energy applied in the proximity of a pacemaker may cause the pacemaker to misdetect signals and trigger heartbeats out of synchronization. Placement of cords of electrosurgical devices, and the power level, mode, and/or current vector at which the electrosurgical energy is applied may further interfere with the operation of the implantable devices.

SUMMARY

Provided in accordance with an embodiment of the present disclosure is an electrosurgical generator. In an aspect of the present disclosure, the electrosurgical generator includes a radio-frequency (RF) output stage configured to output an electrosurgical waveform, a wireless transceiver configured to detect and communicate with an implantable device in a patient, and a controller coupled to the RF output stage and the wireless transceiver, the controller configured to control the RF output stage to generate an electrosurgical waveform based on the implantable device.

In another aspect of the present disclosure, the controller is further configured to determine a type of the implantable device, and control the generation of the electrosurgical waveform by the RF output stage based on the type of the implantable device.

In yet another aspect of the present disclosure, the controller is further configured to calculate a control signal for generating the electrosurgical waveform such that the electrosurgical waveform interlaces with a stimulating waveform generated by the implantable device, and control the generation of the electrosurgical waveform by the RF output stage based on the calculated control signal.

In a further aspect of the present disclosure, the controller calculates the control signal by adjusting at least one of voltage, current, power, duty cycle, repetition rate, frequency, pulse width, or harmonic content of the electrosurgical waveform.

In another aspect of the present disclosure, the wireless transceiver is further configured to receive a status indicator from the implantable device, and wherein the controller is further configured to control the generation of the electrosurgical waveform by the RF output stage based on to the status indicator.

In yet another aspect of the present disclosure, the controller is further configured to cause the wireless transceiver to send, prior to the electrosurgical waveform being output, a data packet to the implantable device to cause the implantable device to switch to a non-operating state, and cause the wireless transceiver to send, after the electrosurgical waveform is output, a data packet to the implantable device to cause the implantable device to switch to a normal operating state.

In still another aspect of the present disclosure, the controller is further configured to cause the wireless transceiver to send a data packet to the implantable device to request a status confirmation of the implantable device.

Provided in accordance with an embodiment of the present disclosure is a method for operating an electrosurgical generator. In an aspect of the present disclosure, the method includes outputting an electrosurgical waveform, detecting and communicating with an implantable device in a patient, and generating an electrosurgical waveform based on the implantable device.

In another aspect of the present disclosure, the method further includes determining a type of the implantable device, and generating the electrosurgical waveform based on the type of the implantable device.

In yet another aspect of the present disclosure, the method further includes calculating a control signal for generating the electrosurgical waveform such that the electrosurgical waveform interlaces with a stimulating waveform generated by the implantable device, and generating the electrosurgical waveform based on the calculated control signal.

In a further aspect of the present disclosure, the control signal is calculated by adjusting at least one of voltage, current, power, duty cycle, repetition rate, frequency, pulse width, or harmonic content of the electrosurgical waveform.

In another aspect of the present disclosure, the method further includes receiving a status indicator from the implantable device, and controlling the generation of the electrosurgical waveform based on to the status indicator.

In yet another aspect of the present disclosure, the method further includes causing the implantable device to switch to a non-operating state prior to the electrosurgical waveform being output, and cause the implantable device to switch to a normal operating state after the electrosurgical waveform is output.

In still another aspect of the present disclosure, the method further includes confirming a status of the implantable device.

Provided in accordance with an embodiment of the present disclosure is an electrosurgical system. In an aspect of the present disclosure, the electrosurgical system includes an electrosurgical tool, an implantable device, and an electrosurgical generator including a radio-frequency (RF) output stage configured to output an electrosurgical waveform, a wireless transceiver configured to detect and communicate with an implantable device in a patient, and a controller coupled to the RF output stage and the wireless transceiver, the controller configured to control the RF output stage to generate an electrosurgical waveform based on the implantable device.

In another aspect of the present disclosure, the controller is further configured to determine a type of the implantable device, and control the generation of the electrosurgical waveform by the RF output stage based on the type of the implantable device.

In yet another aspect of the present disclosure, the controller is further configured to calculate a control signal for generating the electrosurgical waveform such that the electrosurgical waveform interlaces with a stimulating waveform generated by the implantable device, and control the generation of the electrosurgical waveform by the RF output stage based on the calculated control signal.

In a further aspect of the present disclosure, the controller calculates the control signal by adjusting at least one of voltage, current, power, duty cycle, repetition rate, frequency, pulse width, or harmonic content of the electrosurgical waveform.

In another aspect of the present disclosure, the wireless transceiver is further configured to receive a status indicator from the implantable device, and the controller is further configured to control the generation of the electro surgical waveform by the RF output stage based on to the status indicator.

In yet another aspect of the present disclosure, the controller is further configured to cause the wireless transceiver to send, prior to the electrosurgical waveform being output, a data packet to the implantable device to cause the implantable device to switch to a non-operating state, and cause the wireless transceiver to send, after the electrosurgical waveform is output, a data packet to the implantable device to cause the implantable device to switch to a normal operating state.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that embodiments of the present disclosure may be adapted for use with any electrosurgical instrument. It should also be appreciated that different electrical and mechanical connections and other considerations may apply to each particular type of instrument.

Briefly, an electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various electrosurgical instruments (e.g., monopolar instruments, return electrode pads, ultrasonic devices, bipolar electrosurgical forceps, footswitches, etc.). Further, the generator may include electronic circuitry configured to generate radio frequency (RF) energy specifically suited for powering electrosurgical devices operating in various electrosurgical modes (e.g., cut, blend, coagulate, division with hemostasis, fulgurate, spray, etc.) and procedures (e.g., monopolar, bipolar, vessel sealing). The generator is further configured to adjust an RF waveform based on other devices, such as implantable devices, detected in a patient upon whom the electrosurgical procedure is being performed.

Figure 1:
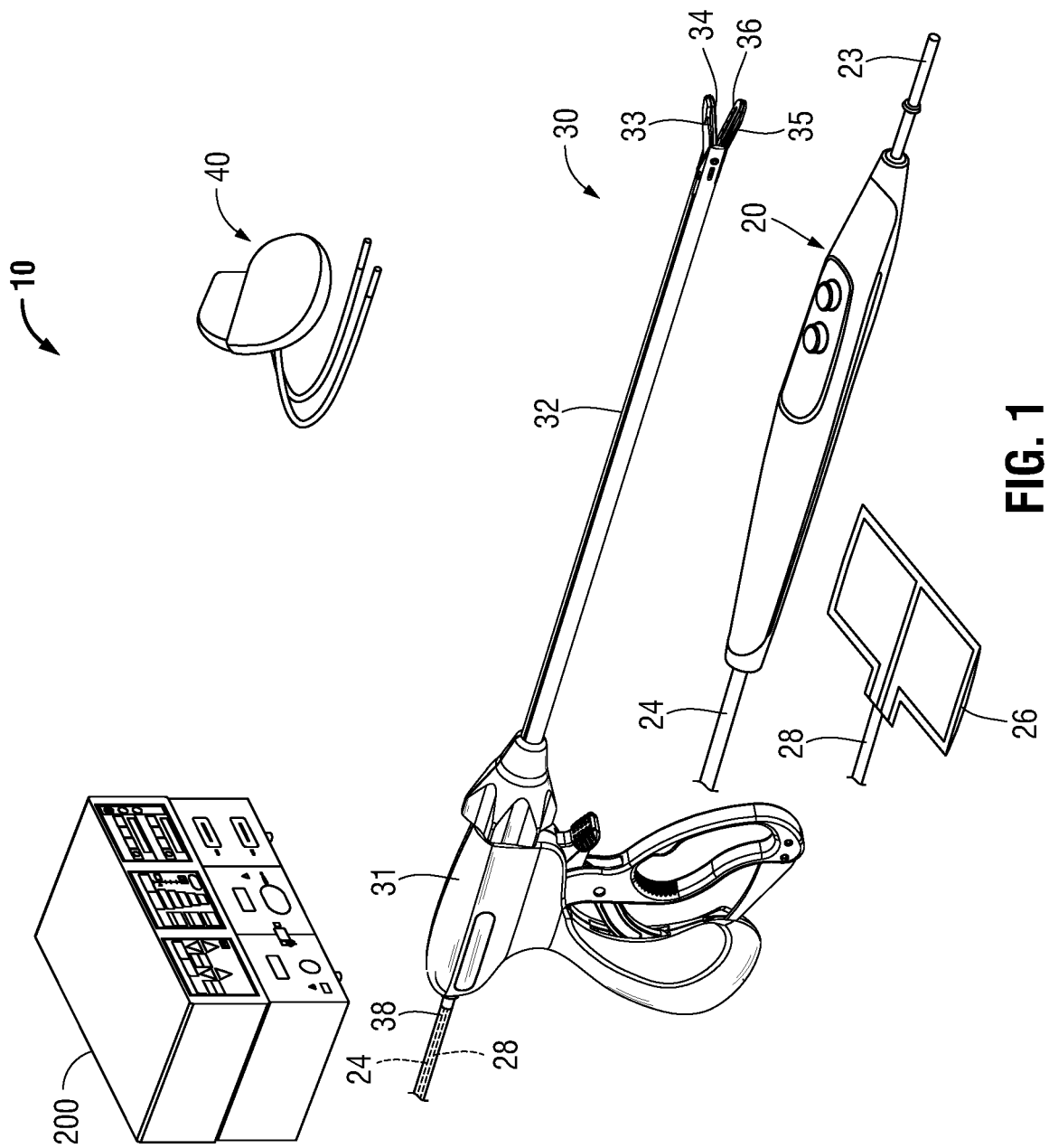
FIG. 1 is a perspective view of an electrosurgical system according to an embodiment of the present disclosure.

Referring to FIG. 1, an electrosurgical system 10 according to the present disclosure includes one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 350 (FIG. 3) of the generator 200, allowing the instrument 20 to cut, coagulate, and/or otherwise treat tissue. The alternating current is returned to the generator 200 through a return electrode pad 26 via a return line 28 at a return terminal 352 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
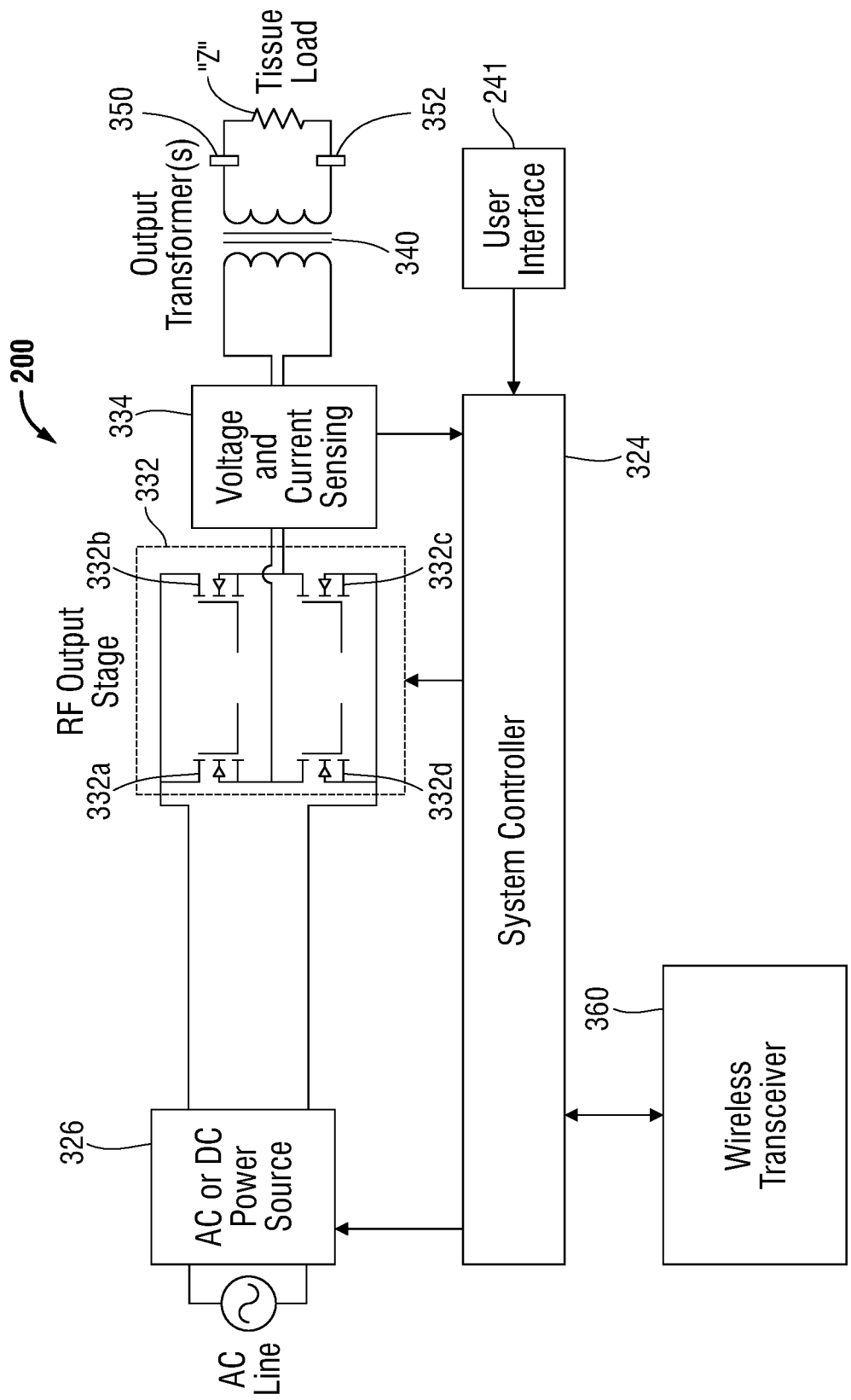
FIG. 3 is a schematic diagram of the electrosurgical generator of FIG. 2.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 350, 352, respectively (FIG. 3). The electrosurgical forceps 30 is coupled to the generator 200 at a port having connections to the active and return terminals 350 and 352 (e.g., pins) via a plug (not shown) disposed at the end of the cable 38, wherein the plug includes contacts from the supply and return lines 24, 28 as described in more detail below.

The system 10 further includes one or more implantable devices 40. Implantable devices 40 may be any type of an implantable device that may be affected by the application of electrosurgical energy to the patient. Implantable devices 40 may include pacemakers, implantable cardiac defibrillators (ICD), and/or implantable neurostimulators. Implantable devices 40 may include a communication interface, such as a wireless transceiver, a radio frequency identification (RFID) chip, and/or any other appropriate communication interfaces known to those skilled in the art. As described further below, generator 200 may detect and/or communicate with implantable device 40 via a wireless transceiver 360 (FIG. 3) in generator 200 and the communication interface included in implantable device 40. In embodiments, wireless transceiver 360 communicates directly with the communication interface included in implantable device 40. In other embodiments, wireless transceiver 360 communicates with the communication interface included in implantable device 40 via an intermediary device, such as a relay device or the like.

Figure 2:
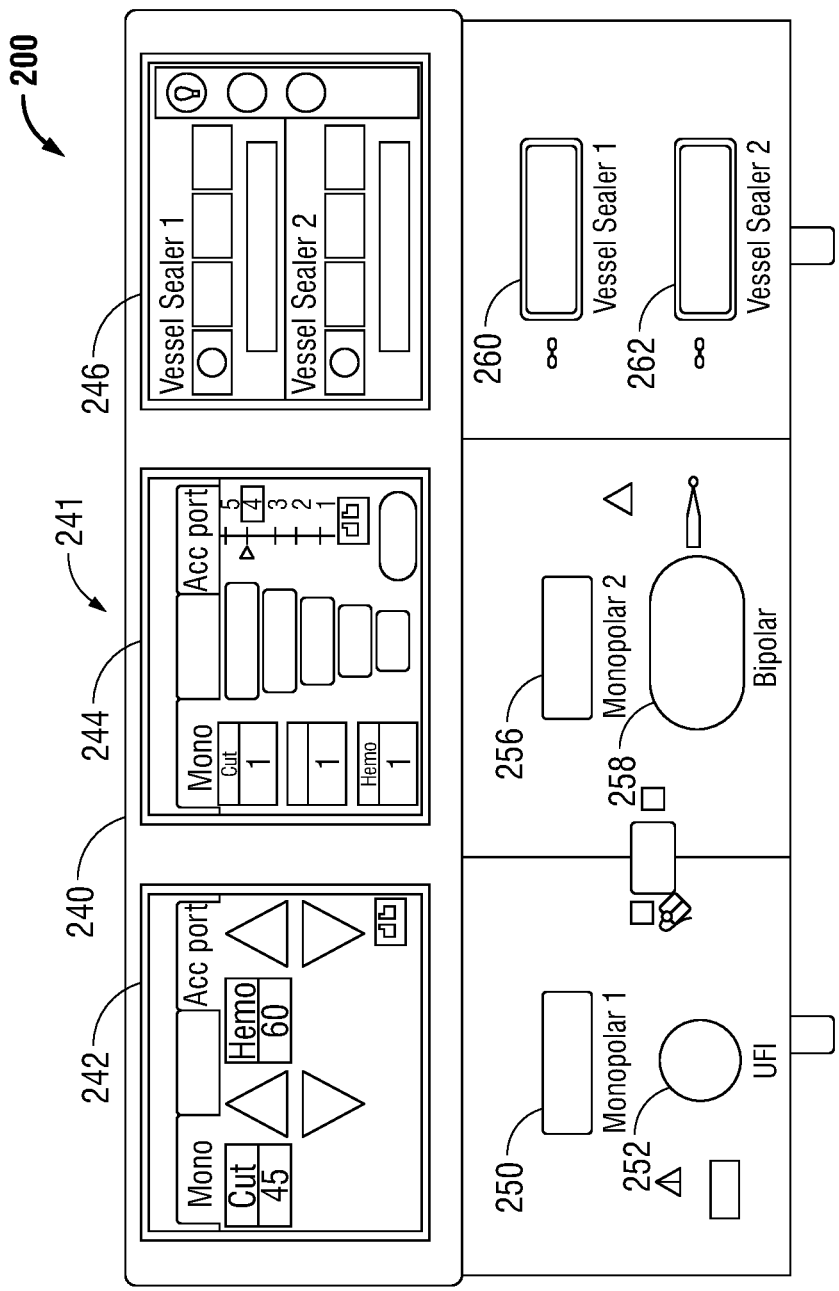
FIG. 2 is a front view of an electrosurgical generator of the electrosurgical system of FIG. 1.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional user inputs (e.g., providing activation of the generator 200). The port 254 is configured to couple to the return electrode pad 26. Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 324 (FIG. 3) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 350 and 352 may be coupled to any of the desired ports 250-262. In embodiments, the active and return terminals 350 and 352 may be coupled to the ports 250-262.

With reference to FIG. 3, the generator 200 also includes a controller 324, a power supply 326, a power converter 332 such as an RF output stage, and a wireless transceiver 360. The power supply 326 may be a high voltage, DC power supply connected to an AC source (e.g., line voltage) and provides high voltage, DC power to the power converter 332, which then converts high voltage, DC power into RF energy and delivers the energy to the active terminal 350. The energy is returned thereto via the return terminal 352. In particular, electrosurgical energy for energizing the monopolar electrosurgical instrument 20 and/or electrosurgical forceps 30 is delivered through the active and return terminals 350 and 352. The active and return terminals 350 and 352 are coupled to the power converter 332 through an isolation transformer 340. The output of power converter 332 transmits current through an isolation transformer 340 to the load "Z", e.g., tissue being treated.

The power converter 332 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 332 may be a resonant RF amplifier or a non-resonant RF amplifier. A non-resonant RF amplifier, as used herein, denotes an amplifier lacking any tuning components, e.g., conductors, capacitors, etc., disposed between the power converter and the load "Z."

The controller 324 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 324 includes output ports that are operably connected to the power supply 326, the power converter 332, and/or the wireless transceiver 360, allowing the controller 324 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 324. The controller 324 then controls the power supply 326 and/or power converter 332, which adjusts power delivered to and/or from the power converter 332, respectively.

The controller 324 may perform various mathematical computations in order to control the power supply 326 and/or power converter 332 to generate an RF waveform having a desired shape, duty cycle, and/or energy content. Examples of computations performed by the controller 324 include, but are not limited to, calculating instantaneous and/or rms power levels, amount of energy delivered on a cycle by cycle basis, load impedance, etc.

The generator 200 according to the present disclosure may also include a plurality of sensors 334. The sensors 334 are coupled to the power converter 332 and may be configured to sense properties of RF energy output by the power converter 332. In embodiments, the generator 200 may also include additional sensors (not shown) coupled to the power supply 326. The controller 324 also receives input signals from the input controls of the generator 200, the instrument 20, the electrosurgical forceps 30, and/or the wireless transceiver 360. The controller 324 utilizes the input signals to adjust power output by the generator 200 and/or performs other control functions thereon.

The power converter 332 includes a plurality of switching elements 332a-332d arranged in an H-bridge topology. In embodiments, power converter 332 may be configured according to any suitable topology including, but not limited to, half-bridge, full-bridge, push-pull, and the like. Suitable switching elements include voltage-controlled devices such as transistors, field-effect transistors (FETs), combinations thereof, and the like.

As described above, the controller 324 is in communication with the power converter 332, in particular, the switching elements 332a-332d. Controller 324 is configured to output a control signal, which may be a pulse-width modulated signal, to switching elements 332a-332d. In particular, controller 324 is configured to modulate a control signal supplied to switching elements 332a-332d of power converter 332. Additionally, controller 324 is configured to calculate power characteristics of generator 200, and control generator 200 based at least in part on the measured power characteristics from the sensors 334. Controller 324 may further calculate and/or adjust the control signal based on signals and/or data received from wireless transceiver 360, as described below.

Figure 4:
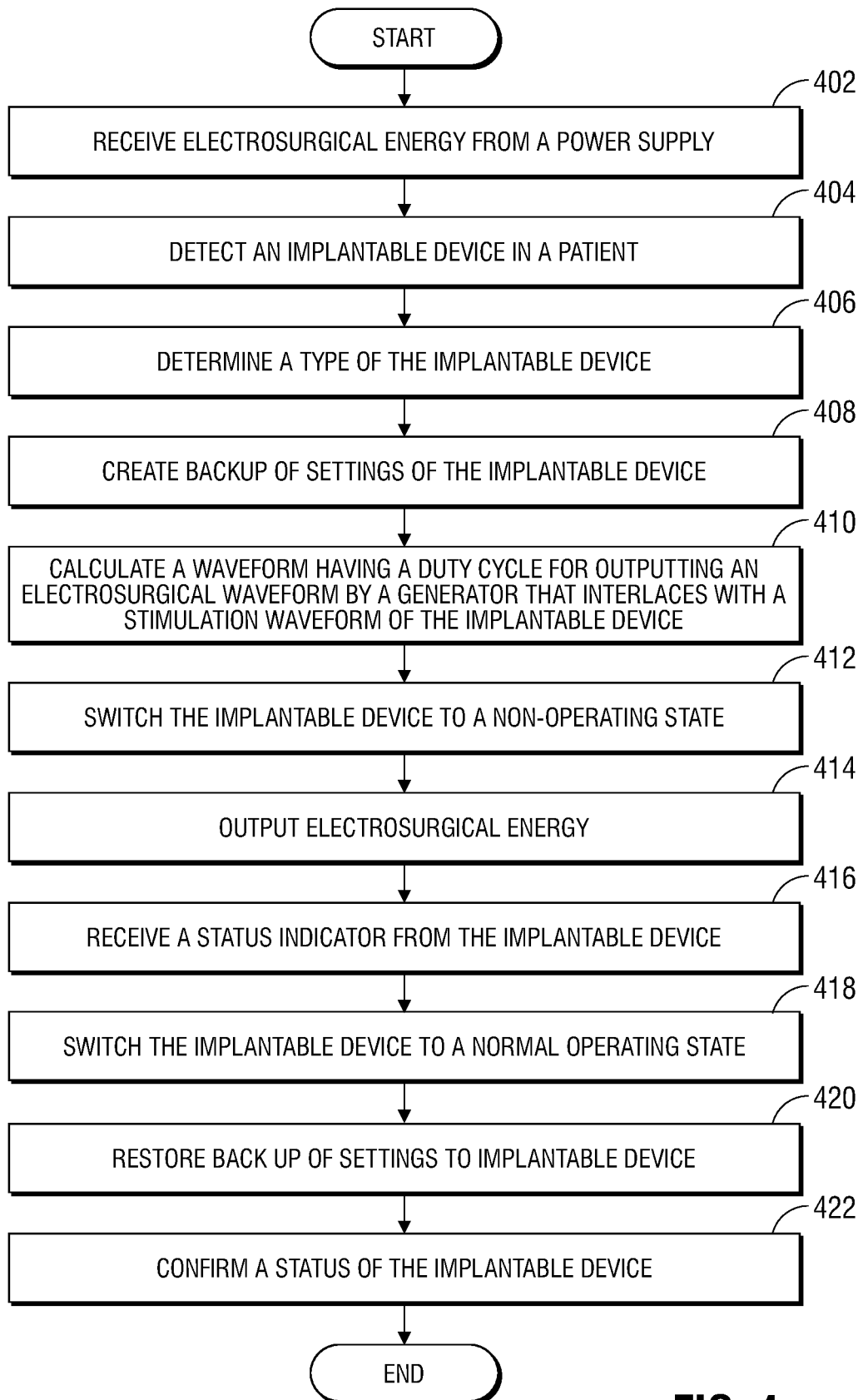
FIG. 4 is a flow chart of a method for operating the electrosurgical generator of FIG. 2.

Turning now to FIG. 4, there is shown a flowchart of an example method of operating a cardiac mode for an electrosurgical generator, such as generator 200. While the following steps of the method are described in a suggested order, those skilled in the art will appreciate that some steps of the method may be performed in a different order, concurrent with other steps, or omitted entirely, without departing from the scope of the present disclosure. The method may begin at step 402 where generator 200 receives electrosurgical energy via power supply 326. As described above, power supply 326 may be connected to a high voltage AC power source and supply DC power to generator 200.

Next, or concurrently therewith, at step 404, wireless transceiver 360 detects whether there are any implantable devices 40 in the patient's body. In embodiments, wireless transceiver 360 may perform a scan to detect if there are any implantable devices 40 within its detectable range and connect to any implantable devices 40 allowing such a connection. In other embodiments, the implantable device 40 may be put into a communications mode by having a magnet placed near the implantable device 40 on the patient's body. Wireless transceiver 360 may then be able to detect and communicate, such as by pairing, with the implantable device 40. Wireless transceiver 360 may detect an implantable device 40 in a patient's body and send a data packet to the detected implantable device 40 to request information from the detected implantable device 40. Wireless transceiver 360 may then receive a data packet including the information requested from the detected implantable device 40.

Thereafter, at step 406, controller 324 may determine a type of the implantable device 40 detected by wireless transceiver 360 at step 404. Controller 324 may then process the information included in the data packet received from the detected implantable device 40 at step 404. In an embodiment, the information may identify the implantable device 40 as a pacemaker. In another embodiment, the information may identify the implantable device 40 as an ICD.

The information may further include data regarding an operating mode of the implantable device 40. In embodiments, a pacemaker may have a normal operating mode of being in a "synchronous mode," i.e., the pacemaker is configured to sense an electrical signal from the patient's heart and produce a stimulation to trigger a heartbeat at the appropriate time, in concert with the patient's normal heart beat. Thus, if the implantable device 40 is a pacemaker, the data regarding the operating mode of the implantable device 40 may inform controller 324 that the pacemaker is operating in a synchronous mode.

A pacemaker may also have an "asynchronous mode," i.e., the pacemaker is configured to produce a stimulation to trigger a heartbeat at a predetermined rate irrespective of the patient's heart's normal heart beat. Thus, when the pacemaker is in the asynchronous mode, the stimulation has a fixed waveform, referred to hereinafter as the stimulation waveform of implantable device 40. The data regarding the operating mode of implantable device 40 may further inform controller 324 of the stimulation waveform.

The information included in the data packet received from implantable device 40 may further include operating settings of the implantable device 40. For example, mode settings, operating settings, calibration settings and/or initial parameters of the implantable device 40 may be included in the data packet. At step 408, generator 200 creates a backup copy of some or all of the data included in the data packet received from implantable device 40 by storing the data in generator 200 prior to the start of the electrosurgical procedure. As described below with reference to step 420, data from this backup may later be restored to the implantable device 40 after the conclusion of the electrosurgical procedure.

Figure 5:
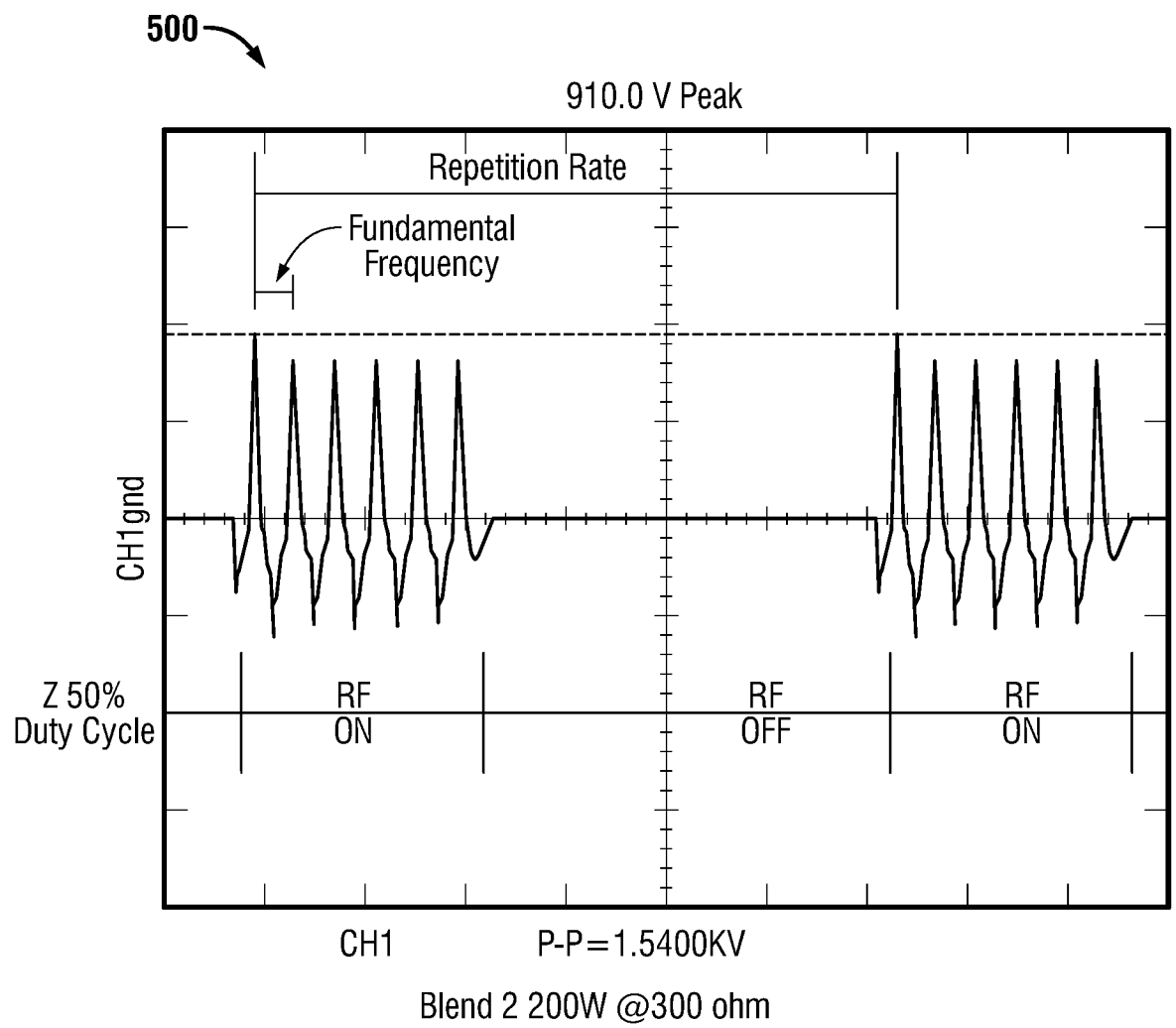
FIG. 5 is a diagram of an exemplary electrosurgical waveform.
Figure 6:
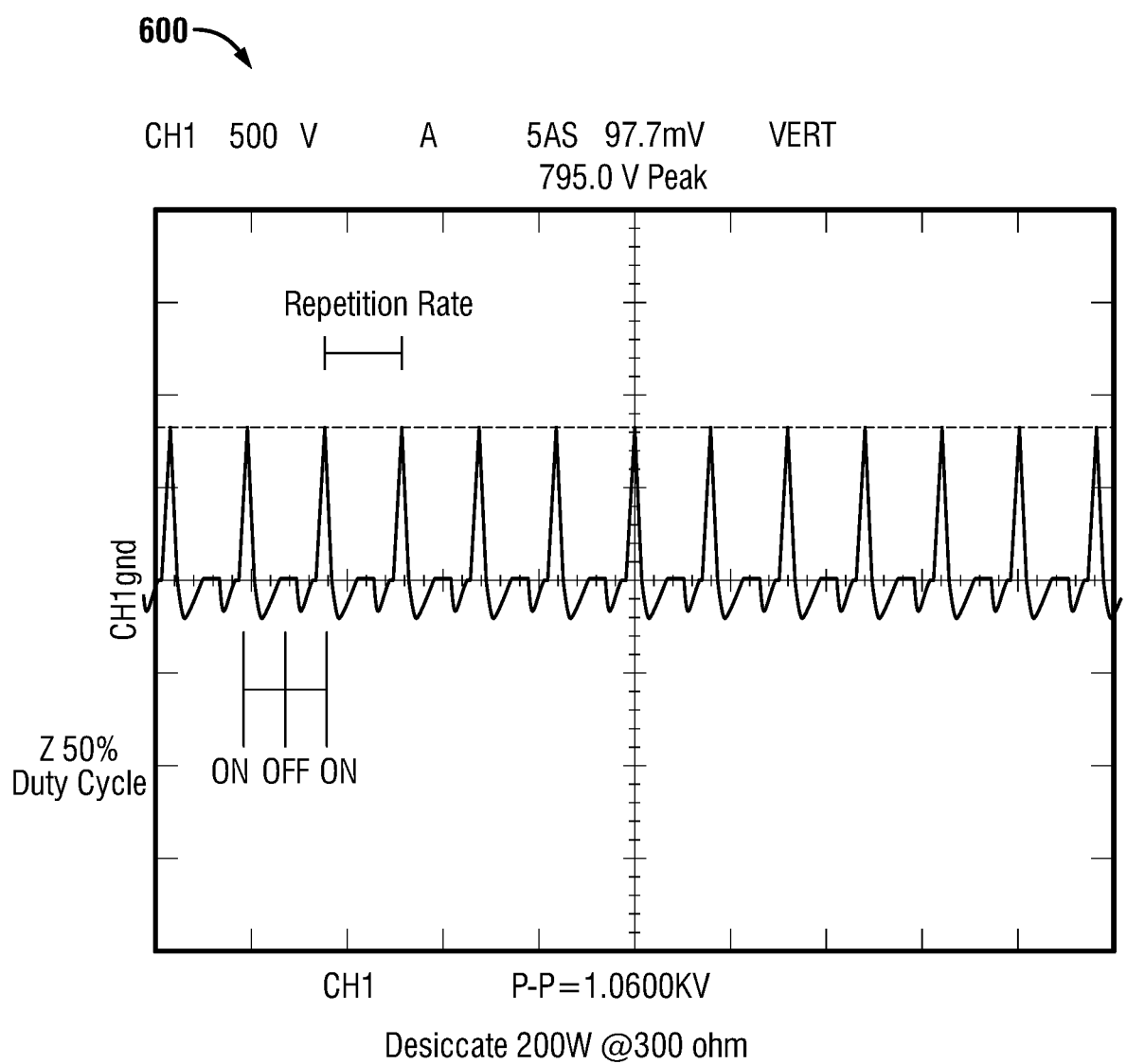
FIG. 6 is another diagram of an exemplary electrosurgical waveform.

Next, at step 410, controller 324 may calculate an electrosurgical waveform for outputting an electrosurgical energy by generator 200. In an embodiment, the electrosurgical waveform calculated by controller 324 may have a duty cycle that interlaces with the stimulation waveform of the implantable device 40. In embodiments, controller 324 may calculate an electrosurgical waveform with a timing of RF signals (i.e. voltage, current, and/or power), amplitude of a peak signal, duty cycle, repetition rate, frequency, pulse width, and/or harmonic content that interlaces with that of the stimulation waveform. An exemplary electrosurgical waveform of a blended type of a coagulation waveform with a 50% duty cycle and voltage spikes of about 910V peak is shown in FIG. 5. Similarly, an exemplary electrosurgical waveform of a desiccating waveform with a 50% duty cycle and voltage spikes of about 795V peak is shown in FIG. 6.

Figure 7:
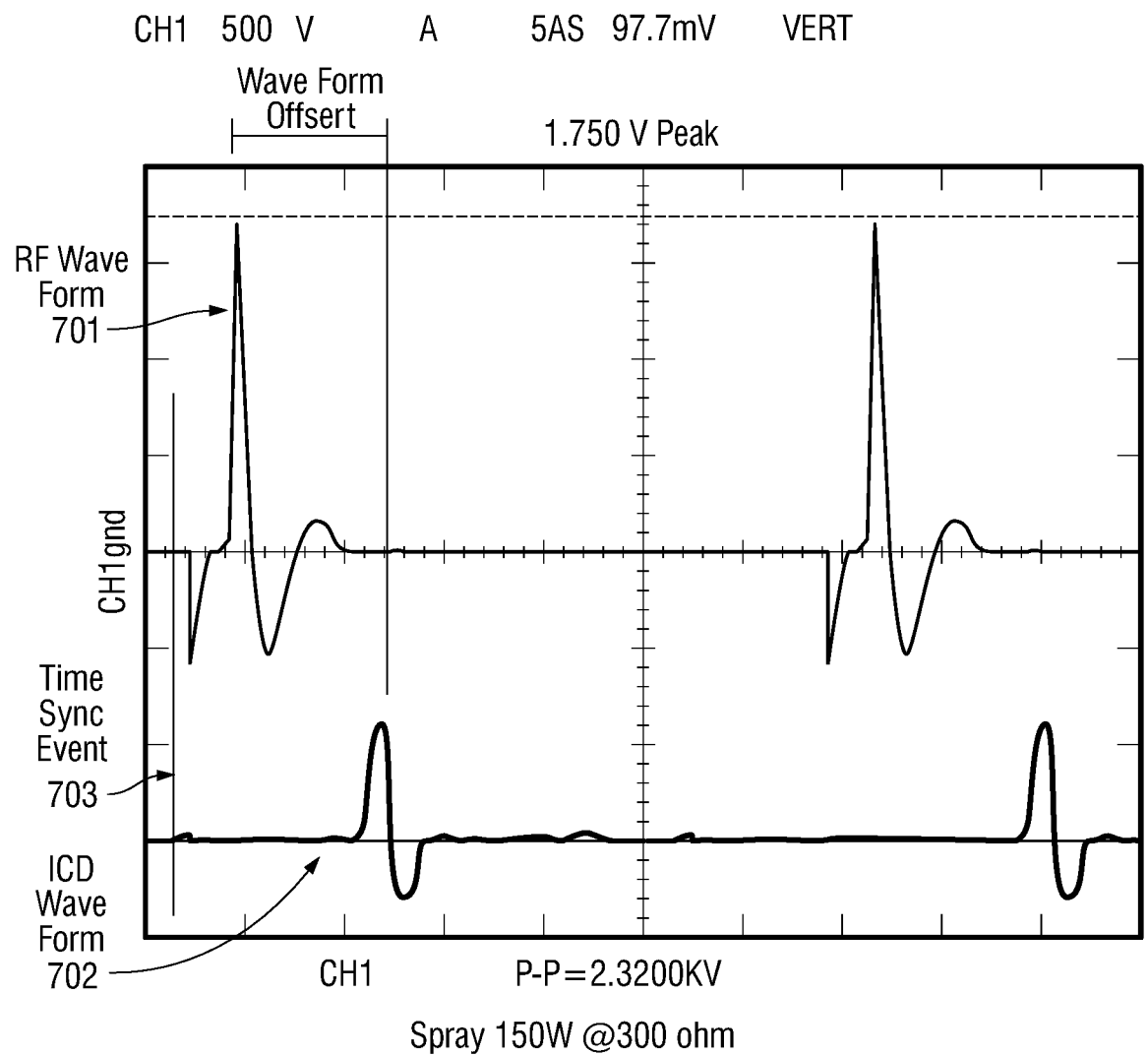
FIG. 7 is yet another diagram of an exemplary electrosurgical waveform.
Figure 8:
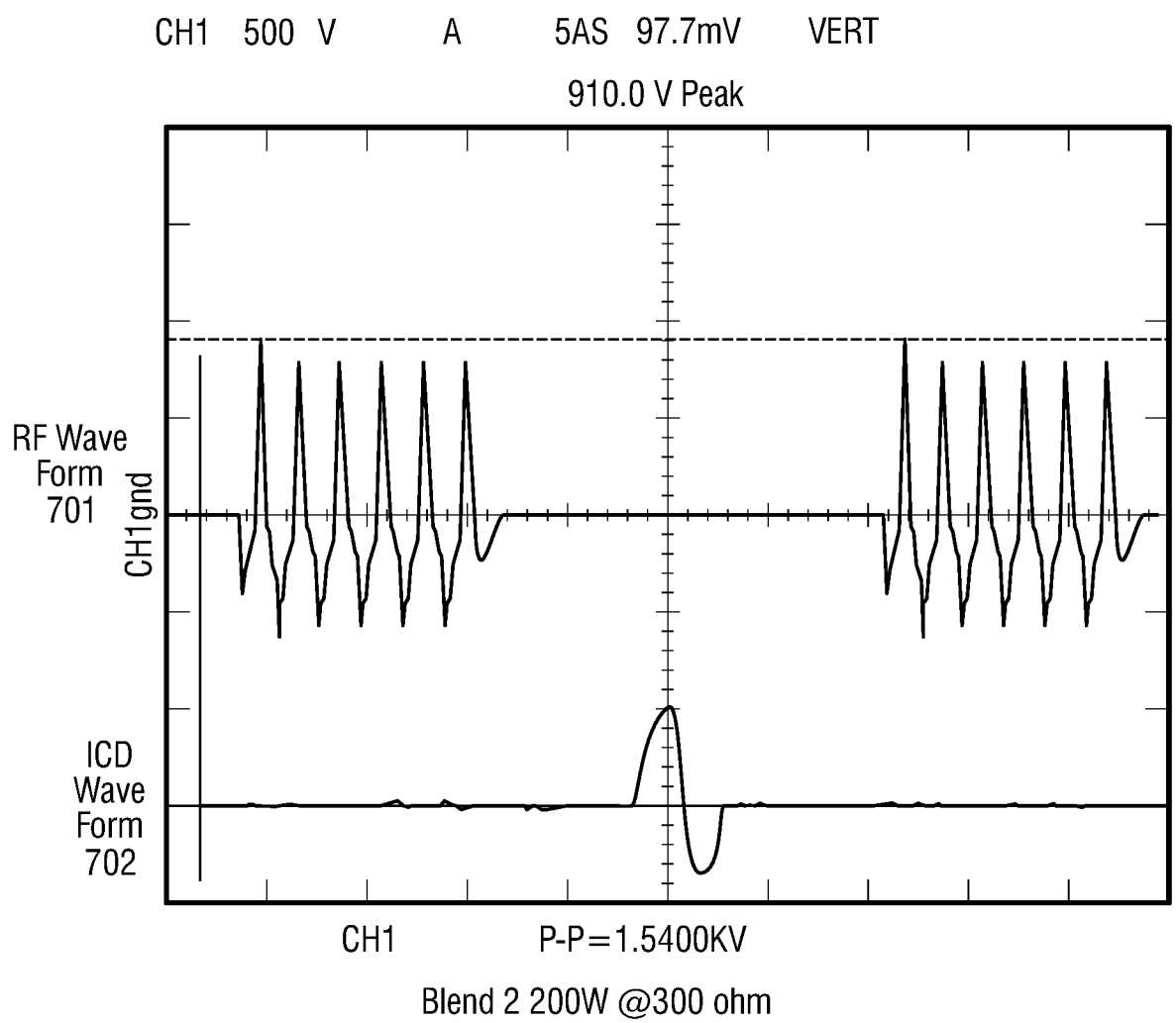
FIG. 8 is still another diagram of an exemplary electrosurgical waveform.

In another embodiment, the electrosurgical waveform calculated by controller 324 may synchronize with the stimulation waveform of implantable device 40, such as to minimize cross-talk interference between generator 200 and implantable device 40. For example, if the detected implantable device 40 is an ICD, controller 324 may calculate an electrosurgical waveform that synchronizes with the simulation waveform of implantable device 40 such that a signal from implantable device 40 occurs at a point in time that is offset from the center frequency of the electrosurgical waveform or other periods of significant RF interference. An exemplary electrosurgical waveform of a coagulation RF waveform that has been synchronized with a stimulation waveform of an ICD is shown in FIG. 7. Likewise, an exemplary electrosurgical waveform that is synchronized with other types of waveforms is shown in FIG. 8.

At step 412, controller 324 signals wireless transceiver 360 to send a data packet to implantable device 40 to cause implantable device 40 to switch to a non-operating state. Controller 324 may automatically signal wireless transceiver 360 to send the data packet to implantable device 40 to cause implantable device 40 to switch to the non-operating state prior to application of electrosurgical energy, and/or controller 324 may signal wireless transceiver 360 after receiving input from a clinician via the user interface of generator 200, described above. In embodiments, prior to starting the electrosurgical procedure, implantable device 40 may have to be switched to a non-operating state, such as to be rendered inactive, switched to an asynchronous mode or RF compatible mode, and/or turned off to avoid damage to implantable device 40, the patient, and/or the clinician performing the electrosurgical procedure. In embodiments where implantable device 40 is an ICD, the application of electrosurgical energy to the patient may cause the ICD to determine incorrectly that the patient is in a fibrillation state causing the ICD to trigger a defibrillation that could potentially injure the patient and/or the clinician. Alternatively, if implantable device 40 is a pacemaker, controller 324 may case wireless transceiver 360 to send a data packet to the pacemaker to cause the pacemaker to switch operating modes, i.e., to switch from the synchronous mode to the asynchronous mode, as described above.

Additionally, there may be periods of time during the electrosurgical procedure during which electrosurgical energy is not applied to the patient. During such periods, the clinician may wish to re-activate an ICD and/or cause a pacemaker to be switched back to the synchronous mode. As such, controller 324 may further be configured to intermittently cause wireless transceiver 360 to send data packets to implantable device 40 to switch implantable device 40 between operating and non-operating states. In embodiments, controller 324 may include a timer to measure a period of time between applications of electrosurgical energy to the patient. If controller 324 determines that a predetermined amount of time, which may be from about 500 milliseconds (ms) to about 10 seconds (s), has expired since electrosurgical energy was last applied to the patient, controller 324 may cause wireless transceiver 360 to send a data packet to implantable device 40 to switch to a normal operating state. Alternatively, the predetermined amount of time may be set by the clinician during setup of generator 200. Similarly, controller 324 may, upon receiving input from the clinician, cause wireless transceiver 360 to send a data packet to implantable device 40 to switch to a normal operating state. Controller 324 may then be further configured to cause wireless transceiver 360 to send another data packet to implantable device 40 to return to the non-operating state prior to electrosurgical energy being applied.

In another embodiment, instead of deactivating implantable device 40, implantable device 40 may be merely instructed by the controller 324 to ignore triggers and/or signals occurring while electrosurgical energy is being applied to the patient. Controller 324 may, prior to electrosurgical energy being applied to the patient, cause wireless transceiver 360 to send a data packet to implantable device 40 to cause implantable device 40 to switch to a passive operating state in which implantable device 40 operates normally but ignores triggers and/or signals received. Then, when electrosurgical energy is no longer being applied to the patient, controller 324 may cause wireless transceiver 360 to send another data packet to implantable device 40 to cause implantable device 40 to switch back to a normal operating state. This may be repeated prior to and after each application of electrosurgical energy to the patient. In embodiments where implantable device 40 is a pacemaker, the pacemaker may be switched to the passive operating mode, i.e., the pacemaker may ignore signals which would cause it to trigger a heartbeat during normal operating mode, but would continue to trigger a heartbeat after a predetermined amount of time has passed, similar to the operation of the asynchronous mode.

In an embodiment where implantable device 40 is an ICD, the ICD may be switched to a state wherein the ICD notifies generator 200 prior to triggering a defibrillation such that application of electrosurgical energy may stop and the clinician standing clear of the patient prior to the defibrillation being triggered. Controller 324 may cause wireless transceiver 324 to send a data packet to implantable device 40 to cause implantable device 40 to switch to a warning state. Then, if implantable device 40 detects that the patient is in a fibrillation state, implantable device 40 sends a data packet to generator 200 to notify controller 324 to stop application of electrosurgical energy to the patient and cause generator 200 to provide a warning, such as an audible, visual, and/or tactile alert, to stand clear of the patient because a defibrillation is about to occur. After the defibrillation, implantable device 40 may send another data packet to generator 200 to notify controller 324 that application of electrosurgical energy may recommence.

At step 414, electrosurgical energy is output to the patient. For example, controller 324 may send a control signal to RF output stage 332 to cause an electrosurgical waveform, such as the waveform calculated at step 408, to be output by generator 200.

Thereafter, at step 416, a status indicator may be received from implantable device 40. Wireless transceiver 360 may receive a data packet from implantable device 40 notifying generator 200 of a status of implantable device 40. As described above, "noise" resulting from the application of electrosurgical energy to the patient may cause interference with the operation of implantable device 40. In particular, application of electrosurgical energy in proximity of a pacemaker or an ICD may cause triggers and/or signals to be misdetected by implantable device 40. To avoid such misdetections, implantable device 40 may notify generator 200 if interference is detected by implantable device 40, e.g., if the noise caused by the application of the electrosurgical energy repeatedly cause implantable device 40 to reach a trigger threshold. Controller 324 may then recalculate the electrosurgical waveform and/or cause implantable device 40 to be switched to a different operating mode to avoid the interference. Controller 324 may modify the calculated electrosurgical waveform by adjusting the timing of the RF signals (e.g., voltage, current, and/or power), the timing of the peak signal, the duty cycle, repetition rate, frequency, pulse width, and/or harmonic content, as described above at step 408.

After the electrosurgical energy has been applied, generator 200 may switch implantable device 40 back to the normal operating state at step 418. Controller 324 may cause wireless transceiver 360 to send a data packet to implantable device 40 to cause implantable device 40 to switch back to the normal operating state, e.g. synchronous mode for a pacemaker. Similar to step 412, controller 324 may automatically cause wireless transceiver 360 to send the data packet to implantable device 40 to cause implantable device 40 to switch back to the normal operating state, and/or controller 324 may cause wireless transceiver 360 to send the data packet after receiving input from the clinician. Generator 200 may further be configured to provide an audible, visual, and/or tactile alert to the clinician after the electrosurgical procedure is completed to remind the clinician to switch implantable device 40 back to the normal operating state. Similarly, an alert may be provided if generator 200 is turned off prior to implantable device 40 being switched back to the normal operating state.

At step 420, generator 200 restores back to implantable device 40 the backup copy of the data that was created at step 408. Generator 200 may be configured to automatically restore the backup data to implantable device 40, and/or may issue an alert to the clinician to remind the clinician that the backup data may need to be restored and await input from the clinician before restoring the backup data to implantable device 40.

Thereafter, at step 422, generator 200 confirms the status of implantable device 40. Controller 324 may cause wireless transceiver 360 to send a data packet to implantable device 40 to request that implantable device 40 send an indication of its operating status to generator 200. Alternatively, or in addition, controller 324 may cause wireless transceiver 360 to send a data packet to implantable device 40 to request that implantable device 40 send a data packet including information regarding the operation of implantable device 40 to generator 200. The data packet may be similar to the data packet received by generator 200 at step 404 and may include mode settings, operating settings, calibration settings and/or initial parameters of implantable device 40. Controller 324 may then compare the information included in the data packet to the information stored in the backup created at step 406. By doing so, generator 200 may confirm that implantable device 40 is switched to the normal operating mode and is functioning correctly after the electrosurgical procedure is completed.

Turning now to FIG. 5, there is shown a diagram of an exemplary electrosurgical waveform 500, according to an embodiment of the present disclosure. Waveform 500 is a blended type of coagulation waveform with a 50% duty cycle (Z), voltage spikes of 910V peak, and a 200 W output.

FIG. 6 shows a diagram of another exemplary electrosurgical waveform 600, according to an embodiment of the present disclosure. Waveform 600 is a desiccating waveform with a 50% duty cycle (Z), voltage spikes of 795V peak, and a 200 W output.

FIG. 7 shows a diagram of another exemplary electrosurgical waveform 701, according to an embodiment of the present disclosure. Waveform 701 is a coagulation waveform that has been synchronized with an ICD waveform 702 at a time sync event 703 which provides a reference point to future timing events.

FIG. 8 shows a diagram of another exemplary electrosurgical waveform 801, according to an embodiment of the present disclosure. Waveform 801 shows synchronizing between other types of waveforms, where a time sync event may be a known reference signal.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical generator, comprising:
   a radio-frequency (RF) output stage configured to output an electrosurgical waveform;
   a wireless transceiver configured to communicate with an implantable device disposed in a patient and configured to generate a stimulating waveform; and
   a controller coupled to the RF output stage and the wireless transceiver, the controller configured to:
      control the RF output stage to generate the electrosurgical waveform based on the implantable device;
      calculate a control signal for generating the electrosurgical waveform such that the electrosurgical waveform interlaces with the stimulating waveform generated by the implantable device; and
      control generation of the electrosurgical waveform by the RF output stage based on the calculated control signal.

2. The electro surgical generator according to claim 1, wherein the controller is further configured to:
   determine a type of the implantable device; and
   control the generation of the electrosurgical waveform by the RF output stage based on the type of the implantable device.

3. The electrosurgical generator according to claim 1, wherein the controller is configured to calculate the control signal by adjusting at least one of voltage, current, power, duty cycle, repetition rate, frequency, pulse width, or harmonic content of the electrosurgical waveform.

4. The electrosurgical generator according to claim 1, wherein the wireless transceiver is further configured to receive a status indicator from the implantable device, and wherein the controller is further configured to control the generation of the electrosurgical waveform by the RF output stage based on the status indicator.

5. The electro surgical generator according to claim 1, wherein the controller is further configured to:
   cause the wireless transceiver to send, prior to the electrosurgical waveform being output, a data packet to the implantable device to cause the implantable device to switch to a non-operating state; and
   cause the wireless transceiver to send, after the electrosurgical waveform is output, a data packet to the implantable device to cause the implantable device to switch to a normal operating state.

6. The electro surgical generator according to claim 1, wherein the controller is further configured to cause the wireless transceiver to send a data packet to the implantable device to request a status confirmation of the implantable device.

7. The electrosurgical generator according to claim 1, wherein the controller is further configured to:
   receive first configuration settings from the implantable device prior to the generation of the electrosurgical waveform;
   create a backup copy of the first configuration settings;
   perform a comparison of the backup copy of the first configuration settings with second configuration settings received from the implantable device after the generation of the electrosurgical waveform; and
   restore the backup copy of the first configuration settings to the implantable device if the comparison indicates that the backup copy of the first configuration settings is different from the second configuration settings.

8. A method for operating an electrosurgical generator, the method comprising:
   outputting an electrosurgical waveform;
   communicating with an implantable device disposed in a patient;
   generating an electrosurgical waveform based on the implantable device;
   generating a stimulating waveform at the implantable device;
   calculating a control signal for generating the electrosurgical waveform such that the electrosurgical waveform interlaces with the stimulating waveform generated by the implantable device; and
   generating the electrosurgical waveform based on the calculated control signal.

9. The method according to claim 8, further comprising:
   determining a type of the implantable device; and
   generating the electrosurgical waveform based on the type of the implantable device.

10. The method according to claim 8, wherein the control signal is calculated by adjusting at least one of voltage, current, power, duty cycle, repetition rate, frequency, pulse width, or harmonic content of the electrosurgical waveform.

11. The method according to claim 8, further comprising:
   receiving a status indicator from the implantable device; and
   controlling a generation of the electrosurgical waveform based on the status indicator.

12. The method according to claim 8, further comprising:
   causing the implantable device to switch to a non-operating state prior to the electrosurgical waveform being output; and
   cause the implantable device to switch to a normal operating state after the electrosurgical waveform is output.

13. The method according to claim 8, further comprising confirming a status of the implantable device.

14. The method according to claim 8, further comprising:
   receiving first configuration settings from the implantable device prior to the electrosurgical waveform being generated;
   creating a backup copy of the first configuration settings;
   performing a comparison of the backup copy of the first configuration settings with second configuration settings received from the implantable device after the electrosurgical waveform is generated; and
   restoring the backup copy of the first configuration settings to the implantable device if the comparison indicates that the backup copy of the first configuration settings is different from the second configuration settings.

15. An electrosurgical system comprising:
   an electrosurgical tool;
   an implantable device configured to generate a stimulating waveform; and
   an electrosurgical generator including:
      a radio-frequency (RF) output stage configured to output an electrosurgical waveform;
      a wireless transceiver configured to communicate with an implantable device disposed in a patient; and
      a controller coupled to the RF output stage and the wireless transceiver, the controller configured:
         control the RF output stage to generate the electrosurgical waveform based on the implantable device;
         calculate a control signal for generating the electrosurgical waveform such that the electrosurgical waveform interlaces with the stimulating waveform generated by the implantable device; and
         control generation of the electrosurgical waveform by the RF output stage based on the calculated control signal.

16. The electrosurgical system according to claim 15, wherein the controller is further configured to:
   determine a type of the implantable device; and
   control the generation of the electrosurgical waveform by the RF output stage based on the type of the implantable device.

17. The electrosurgical system according to claim 15, wherein the controller is configured to calculate the control signal by adjusting at least one of voltage, current, power, duty cycle, repetition rate, frequency, pulse width, or harmonic content of the electrosurgical waveform.

18. The electrosurgical system according to claim 15, wherein the wireless transceiver is further configured to receive a status indicator from the implantable device, and wherein the controller is further configured to control the generation of the electrosurgical waveform by the RF output stage based on the status indicator.

19. The electrosurgical system according to claim 15, wherein the controller is further configured to:
   cause the wireless transceiver to send, prior to the electrosurgical waveform being output, a data packet to the implantable device to cause the implantable device to switch to a non-operating state; and
   cause the wireless transceiver to send, after the electrosurgical waveform is output, a data packet to the implantable device to cause the implantable device to switch to a normal operating state.

* * * * *